US00PP25993P2

(12) United States Plant Patent
Kordes

(10) Patent No.: US PP25,993 P2
(45) Date of Patent: Oct. 20, 2015

(54) FLORIBUNDA ROSE PLANT NAMED 'KORTEKCHO'

(50) Latin Name: *Rosa hybrida*
Varietal Denomination: KORtekcho

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co KG, Offensoth-Sparfeshoop (DE)

( * ) Notice: Subject to any disclaimer, the term of this patent is extended or adjusted under 35 U.S.C. 154(b) by 194 days.

(21) Appl. No.: 13/998,459

(22) Filed: Nov. 1, 2013

(51) Int. Cl.
*A01H 5/02* (2006.01)

(52) U.S. Cl.
USPC ..... Plt./148

(58) Field of Classification Search
USPC ..... Plt./148
See application file for complete search history.

*Primary Examiner* — Anne Grunberg

(57) ABSTRACT

A new and distinct variety of rose with long lasting, novel pink flowers, and attractive foliage with excellent disease resistance. It exhibits bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORtekcho'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2003. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORtekcho'.

SUMMARY OF THE INVENTION

The new rose plant may be distinguished from its seed parent, an un-named seedling, by the following combination of characteristics:

1. 'KORtekcho' has a moderately vigorous growth habit, whereas the un- named seedling has a vigorous growth habit.
2. 'KORtekcho' has excellent disease resistance, whereas the un-named seedling has average disease resistance.

The new rose plant may be distinguished from its pollen parent, an un-named seedling, by the following combination of characteristics:

1. 'KORtekcho' has a strong fragrance, whereas the un-named seedling has a slight fragrance.
2. 'KORtekcho' has a very double petal count, whereas the un-named seedling has a semi-double petal count.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORtekcho' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORtekcho' was selected in May 2004 from the seedling beds to be asexually propagated for further evaluation. The first asexual propagation of 'KORtekcho' was done by budding in July 2004 at the inventor's nursery in Offenseth-Sparrieshoop, Germany.

These initial and other subsequent propagations conducted in controlled environments demonstrate that 'KORtekcho' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORtekcho'.

DETAILED BOTANICAL DESCRIPTION

The following is a description of 'KORtekcho', as observed growing in October 2013 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORsouba', a rose variety from the same inventor described and illustrated in U.S. Plant Pat. No. 21,247 and issued on Aug. 31, 2010 are compared to 'KORtekcho' in Chart 1.

CHART 1

| Characteristic | 'KORtekcho' | 'KORsouba' |
|---|---|---|
| Flower color | Pink | Cream pink |
| Number of leaflets per leaf | 7 | 3-5 |
| Receptacle shape | Funnel-shaped | Pear-shaped |

Parents:

*Seed parent*.—An un-named seedling.

*Pollen parent*.—An un-named seedling.

Classification:

*Botanical classification*.—*Rosa hybrida* 'KORtekcho'.

*Commercial classification*.—Floribunda rose.

FLOWER AND FLOWER BUD

Blooming habit: Recurrent. Floriferous.

Flower bud:

*Size*.—Upon opening, 45 mm in length from base of receptacle to distal end of bud and 45 mm diameter at its widest point.

*Bud form*.—Short. Pointed ovoid.

*Bud color*.—As sepals first unfold, bud color is Red-Purple Group 59D. When ¼ open, the upper surface of petals is Red-Purple Group N66D, and the lower surface is Red-Purple Group 69C with marginal area Red-Purple Group N66D.

*Sepals*.—Color: Upper surface Yellow-Green Group 146D. Lower surface Yellow-Green Group 146C. Intonations of Greyed-Orange Group 166D along the center of the sepal. Size: Average 20 mm (l)×12 mm (w). Shape: Very weak foliaceous appendages on 1-3 of the five sepals. Apex: Apiculate. Base: Flat at union with receptacle. Quantity: Five. Surface texture: Upper side: Very pubescent. Lower surface: Lightly pubescent. Margins: Pubescent with moderate stipitate glands.

Flower bloom:

*Fragrance*.—Strong with citron, elderberry and fruit notes.

*Duration*.—On the plant 4-7 days. Senesced petals drop away cleanly.

*Size*.—Medium for a floribunda rose. When open, the average flower diameter is 75 mm and the average flower height is 55 mm.

*Form*.—Shape of flower when viewed from the side: Upon opening, upper part: Flat. Upon opening, lower part: Flattened convex. Open flower, upper part: Convex. Open flower, lower part: Flattened convex.

Color:

*Upon opening, petals*.—Outermost petals: Outer Side: Red-Purple Group 69D with marginal area Red-Purple Group N66D. Inner Side: Red-Purple Group N66D. Innermost petals: Outer Side: Red-Purple Group 70D. Inner Side: Red-Purple Group 73B.

*Upon opening, basal petal spots*.—Basal petal spot, outermost petals: Outer Side: Green-Yellow Group 1B. Inner Side: Green-Yellow Group 1C. Basal petal spot, innermost petals: Outer Side: Yellow Group 3B. Inner Side: Yellow Group 9B.

*After opening, petals*.—Outermost petals: Outer Side: Purple Group 75C. Inner Side: Purple Group 75B with intonations of Red-Purple Group 67B. Innermost petals: Outer Side: Red-Purple Group N66D. Inner Side: Red-Purple Group N66D.

*After opening, basal petal spots*.—Basal petal spot, outermost petals: Outer Side: Green-Yellow Group 1C. Inner Side: Green-Yellow Group 1C. Basal petal spot, innermost petals: Outer Side: Green-Yellow Group 1C. Inner Side: Green-Yellow Group 1B.

General tonality: On open flower Red-Purple Group 73B. No change in the general tonality at the end of the 5$^{th}$ day. Afterwards, general tonality is Red-Purple Group 62C.

Petals:

*Petal count*.—Very Double.

*Average range*.—Approximately 75 petals under normal conditions.

*Petal reflex*.—Petals slightly reflexed.

*Petal margin*.—Entire.

*Petal shape*.—Obovate. Apex: Obtuse. Base: Cuneate.

*Petal size*.—40-45 mm (l)×30-40 mm (w).

*Thickness*.—Thin.

*Petal arrangement*.—Quartered.

*Texture*.—Smooth.

Petaloids:

*Petaloid count*.—Average of 5-7 per flower.

*Petaloid size*.—12-30 mm (l)×5-20 mm (w).

*Petaloid color*.—Inner side: Red-Purple Group 69C with marginal area Red-Purple Group N66C. Outer side: Red-Purple Group 69C with marginal area Red-Purple Group N66C.

*Petaloid texture*.—Smooth.

*Margins*.—Entire to undulated.

*Petaloid shape*.—Most commonly spatulate to elliptical, with some petaloids highly irregular. Apex: Obtuse. Base: Attenuate.

Reproductive organs:

*Pistils*.—Average. Approximately 40 present. Stigmas: Location: Superior in position to anthers. Color: Greyed-Yellow Group 160C with intonations of Red Group 46C. Styles: Length: About 12 mm long. Color: Greyed-Yellow Group 160C with intonations of Red Group 46C.

*Stamens*.—Approximately 50 on average and regularly arranged. Anthers: Size: Average 3 mm (l)×1 mm (w). Color: Greyed-Orange Group 163B. Pollen: Generally present. Color: Greyed-Orange Group 163A. Filaments: Color: Greyed-Yellow Group 160D with intonations of Greyed-Red Group 179C at base of filament. Length: 10 mm.

*Receptacle*.—Surface: Lightly pubescent. Color: Yellow-Green Group 146B. Shape: Funnel-shaped. Texture: Smooth. Size: 12 mm (h)×9 mm (w).

*Pedicel*.—Length: 30-60 mm average length. Diameter: 3.5-5 mm average diameter. Color: Yellow-Green Group 146D with strong intonations of Greyed-Red Group 181A. Strength: Somewhat strong. Texture: Smooth. Borne: Multiple flower buds per stem, generally 1 to 4. Flowers pendant.

*Peduncle*.—Length: 10-30 mm average length. Diameter: 3-4 mm average diameter. Color: Yellow-Green Group 146C with intonations of Greyed-Orange Group 174B. Strength: Strong. Texture: Smooth.

THE PLANT

Growth: Moderately vigorous.

Plant habit: Bushy. When grown as a field plant, the average plant height is 100 cm and the average plant width is 50 cm.

Stems:

*Stem color*.—Young wood: Yellow-Green Group 146C. Older wood: Yellow-Green Group 146A.

*Intonations*.—Greyed-Red Group 181C.

*Stem surface texture*.—Young wood: Smooth. Older wood: Rough.

Prickles: Present.

*Incidence*.—Average of 10 per each 10 cm of stem.

*Size*.—Average length: 8-10 mm. Very small prickles less than 2 mm in length also present.

*Color*.—Immature prickles: Greyed-Red Group 181A. Mature prickles: Greyed-Orange Group 164A. Senescing to Greyed -Brown Group 199A.

*Shape*.—Concave.

Leaves: Normally 7 leaflets on normal leaves in middle of the stem.

*Venation pattern*.—Pyramidal net pattern.

*Leaf size*.—130-170 mm (l)×110-130 mm (w).

*Abundance*.—Average.

Leaflets:

*Size*.—Average size of the terminal leaflet is 65 mm (l)×50 mm (w).

*Shape*.—Ovate. Base: Obtuse. Apex: Acute.

*Margins*.—Serrated.

*Surface*.—Upper side of leaflet: Semi-glossy. Under side of leaflet: Matte.

*Texture*.—Upper side of leaflet: Leathery. Under side of leaflet: Leathery.

*Color, mature foliage*.—Upper Leaflet Surface: Yellow-Green Group 146A. Lower Leaflet Surface: Yellow-Green Group 147C.

*Color, juvenile foliage*.—Upper Leaflet Surface: Yellow-Green Group 146B. Lower Leaflet Surface: Yellow-Green Group 147C.

*Anthocyanin intonation*.—Greyed-Purple Group 183B and Greyed-Purple Group 183C. Location: Variable from just leaf margins to entire leaf surface of juvenile foliage.

*Arrangement*.—Odd pinnate.

*Venation*.—Reticulate.

Stipules:

*Size*.—25 mm (l)×10 mm (w).

*Stipule color*.—Yellow-Green Group 46D and Yellow-Green Group 46B.

*Anthocyanin*.—Greyed-Purple Group 185C in the center of stipule on both the upper and lower surfaces.

*Stipitate glands*.—Abundant numbers along margins.

*Prickles*.—Often a small prickle on lower side.

*Texture*.—Smooth.

*Shape*.—Apex: Apiculate. Base: Slightly winged.

Petiole:

*Length*.—Average 15 mm.

*Diameter*.—Average 3 mm.

*Petiole color*.—Yellow-Green Group 146C. Underneath: Yellow-Green Group 146C.

*Margins*.—Limited numbers of stipitate glands.

*Anthocyanin*.—Greyed-Purple Group 185D on upper side.

*Prickles*.—Present.

*Texture*.—Smooth.

Petiole rachis:

*Length*.—Average 20-30 mm.

*Diameter*.—Average 2-3 mm.

*Color*.—Yellow-Green Group 146D. Anthocyanin present on juvenile tissue: Greyed-Purple Group 185C.

*Margins*.—Limited numbers of stipitate glands.

*Prickles*.—A few small prickles underneath.

Hips/seed formation: None observed.

Winter hardiness: Unknown.

Disease resistance: Excellent resistance to Powdery mildew (*Sphaerotheca pannosa*), blackspot (*Diplocarpon rosae*), and rust (*Phragmidium* sp.) diseases under normal growing conditions in Jackson County, Oreg.

I claim:

1. A new and distinct variety of rose plant, as described and illustrated herein.

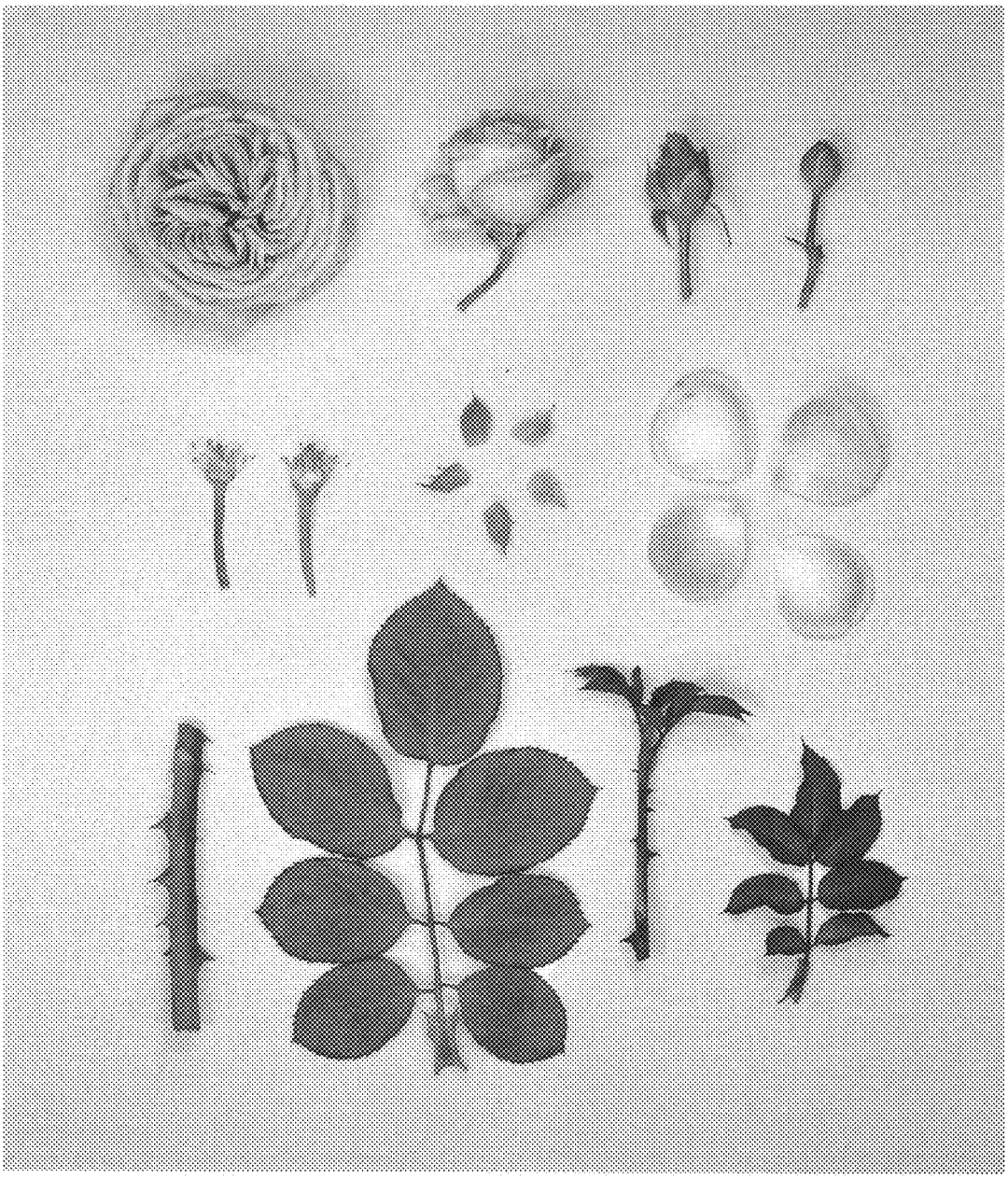

* * * * *